United States Patent
Castelazo

(10) Patent No.: US 10,681,940 B2
(45) Date of Patent: Jun. 16, 2020

(54) BREAST SUPPORT

(71) Applicant: Catherine Carla Castelazo, Westlake Village, CA (US)

(72) Inventor: Catherine Carla Castelazo, Westlake Village, CA (US)

(*) Notice: Subject to any disclaimer, the term of this patent is extended or adjusted under 35 U.S.C. 154(b) by 0 days.

(21) Appl. No.: 16/114,066

(22) Filed: Aug. 27, 2018

(65) Prior Publication Data
US 2019/0059457 A1 Feb. 28, 2019

Related U.S. Application Data

(60) Provisional application No. 62/550,059, filed on Aug. 25, 2017.

(51) Int. Cl.
| | |
|---|---|
| *A41C 3/00* | (2006.01) |
| *A45D 44/22* | (2006.01) |
| *A61F 13/02* | (2006.01) |
| *A61F 5/40* | (2006.01) |
| *A47C 20/02* | (2006.01) |
| *A41C 3/14* | (2006.01) |
| *A41C 3/12* | (2006.01) |

(52) U.S. Cl.
CPC .............. *A41C 3/005* (2013.01); *A45D 44/22* (2013.01); *A47C 20/02* (2013.01); *A61F 5/40* (2013.01); *A61F 13/02* (2013.01); *A41C 3/12* (2013.01); *A41C 3/144* (2013.01)

(58) Field of Classification Search
CPC ................................ A41C 3/005; A45D 44/22
USPC ........................................................ 450/81, 88
See application file for complete search history.

(56) References Cited

U.S. PATENT DOCUMENTS

| | | | | |
|---|---|---|---|---|
| 2,793,369 A | * | 5/1957 | Panighini ............... | A41C 3/065 450/53 |
| 5,716,255 A | * | 2/1998 | Abercrombie ........... | A41C 3/12 2/267 |
| 8,047,892 B1 | * | 11/2011 | Dempsey ............... | A41C 3/005 450/54 |
| 9,622,515 B1 | * | 4/2017 | Dietz ..................... | A41C 3/005 |

* cited by examiner

*Primary Examiner* — Gloria M Hale

(57) ABSTRACT

A breast support has a support body with an upper support portion and a sternum portion, as well as a pair of breast supports. The upper support portion is connected above the sternum portion, and the breast supports are connected to the sides of the sternum portion. An adhesive layer on a rear side of the support body allows the support body to be affixed to a user's chest. The upper support portion has two lateral support portions, each with a plurality of ridges for enhanced support.

7 Claims, 4 Drawing Sheets

BREAST SUPPORT

The current application claims a priority to the U.S. Provisional Patent application Ser. No. 62/550,059 filed on Aug. 25, 2017. The current application is filed on Aug. 27, 2018, whereas Aug. 25, 2018 and Aug. 26, 2018 were on a weekend.

FIELD OF THE INVENTION

The present invention relates generally to cosmetic and wearable apparatuses. More particularly, the present invention relates to breast support apparatuses.

BACKGROUND OF THE INVENTION

The present invention is an improvement to current breast patch technologies that claim to help prevent the onset of wrinkles between the breasts. The current technologies can be improved by changing the hardness and tensile strength of the material so that the skin is best supported from creasing which causes wrinkles.

There is a need for a technology that can be worn either or both during the day and night. The strapless sticky bra has proven its ability to comfortably adhere to the chest. There is a need for a technology that is a combination of the sticky bra polymer that comfortably sticks to the skin, and a structurally supportive material that is affixed to the other side of the polymer that supports the skin of the chest from wrinkling. There is a need for a way that people can use to help their chest fight the force of gravity that cause wrinkles to their chest while they sleep.

DETAIL DESCRIPTIONS OF THE INVENTION

All illustrations of the drawings are for the purpose of describing selected versions of the present invention and are not intended to limit the scope of the present invention. The present invention is to be described in detail and is provided in a manner that establishes a thorough understanding of the present invention. There may be aspects of the present invention that may be practiced or utilized without the implementation of some features as they are described. It should be understood that some details have not been described in detail in order to not unnecessarily obscure focus of the invention. References herein to "the preferred embodiment", "one embodiment", "some embodiments", or "alternative embodiments" should be considered to be illustrating aspects of the present invention that may potentially vary in some instances and should not be considered to be limiting to the scope of the present invention as a whole.

The present invention is a reusable breast support technology intended to preserve and/or enhance the cosmetic beauty of a user's skin by preventing formation of wrinkles on the skin between the user's breasts. The present invention is an improvement upon breast patches that are made of a polymer, such as silicon or other rubber plastics. The present invention is more structurally sound compared to other breast enhancement technologies in that it helps keep the skin from folding at the sternum between the breasts. In the preferred embodiment, the present invention is formed from a solid yet flexible material, articulating with the skin of the user. The breast support of the present invention may be manufactured through any currently known or new methods, such as, but not limited to, 3D printing, polymer casting, and any other methods, currently known to those in the art of polymer solid manufacturing or other relevant manufacturing methods or means. Furthermore, in some embodiments, a polymer such as silicone is affixed to the backside of the component where it will keep the material safely bound to the skin and can be removed by peeling off the present invention from the user's torso similar to the "sticky bras" that are used today. Once the present invention is properly and comfortably placed on the user's torso, then the present invention may be brushed or patted on by the user's hand(s) so that the polymer is optimally affixed to the wearer.

The present invention may be enclosed in a reusable container that may match the shape and be able to fit the present invention in a cast where the polymer component that adheres to the skin will not be able to adhere to lint, hair, or other materials when the present invention is not worn. The present invention may be cleaned with soap and water, or similar typical cleaning methods. The dimensions of the present invention may vary in size in order to properly conform to varying anatomy of different users.

Figure 1:
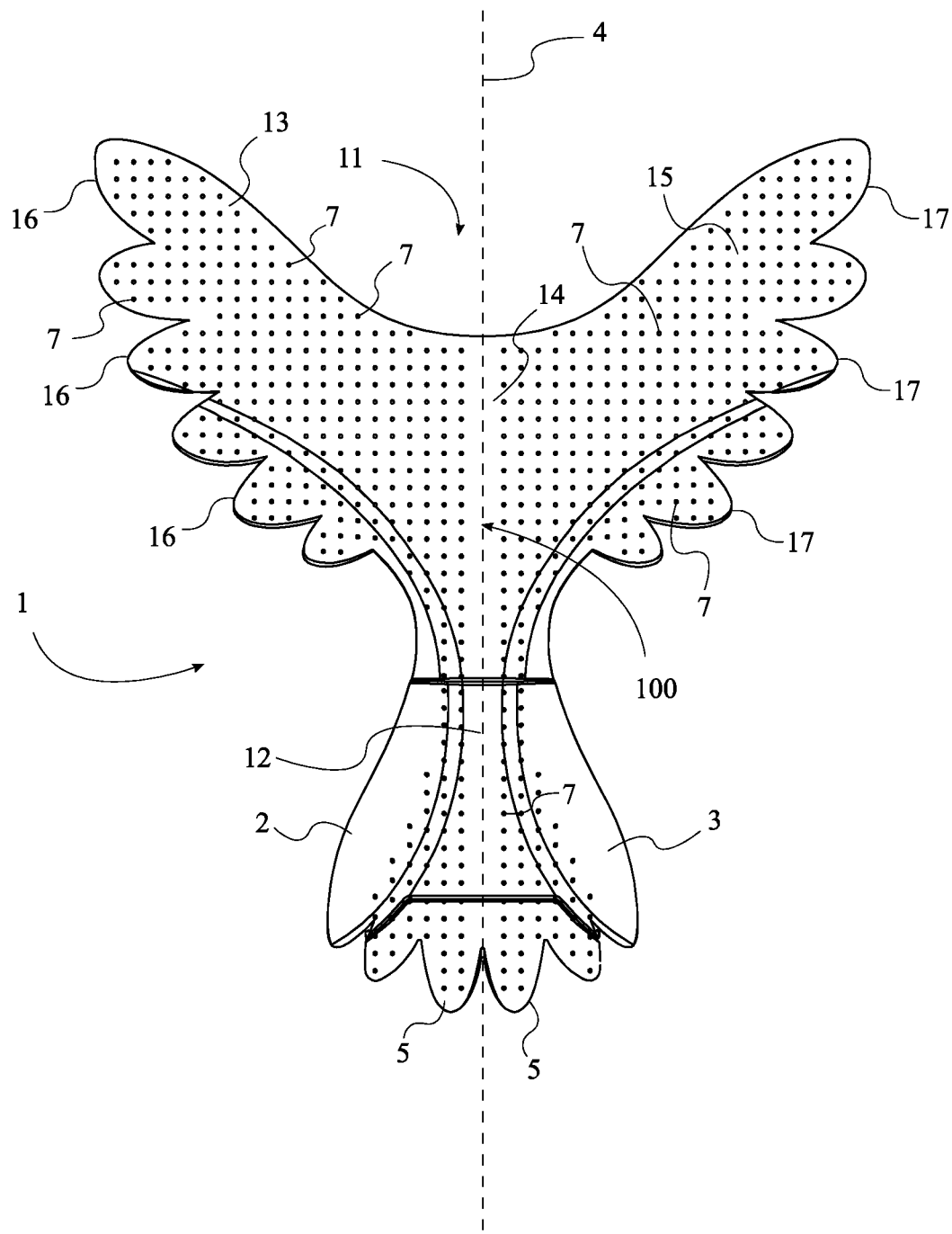
FIG. 1 is a front view of the present invention.
Figure 2:
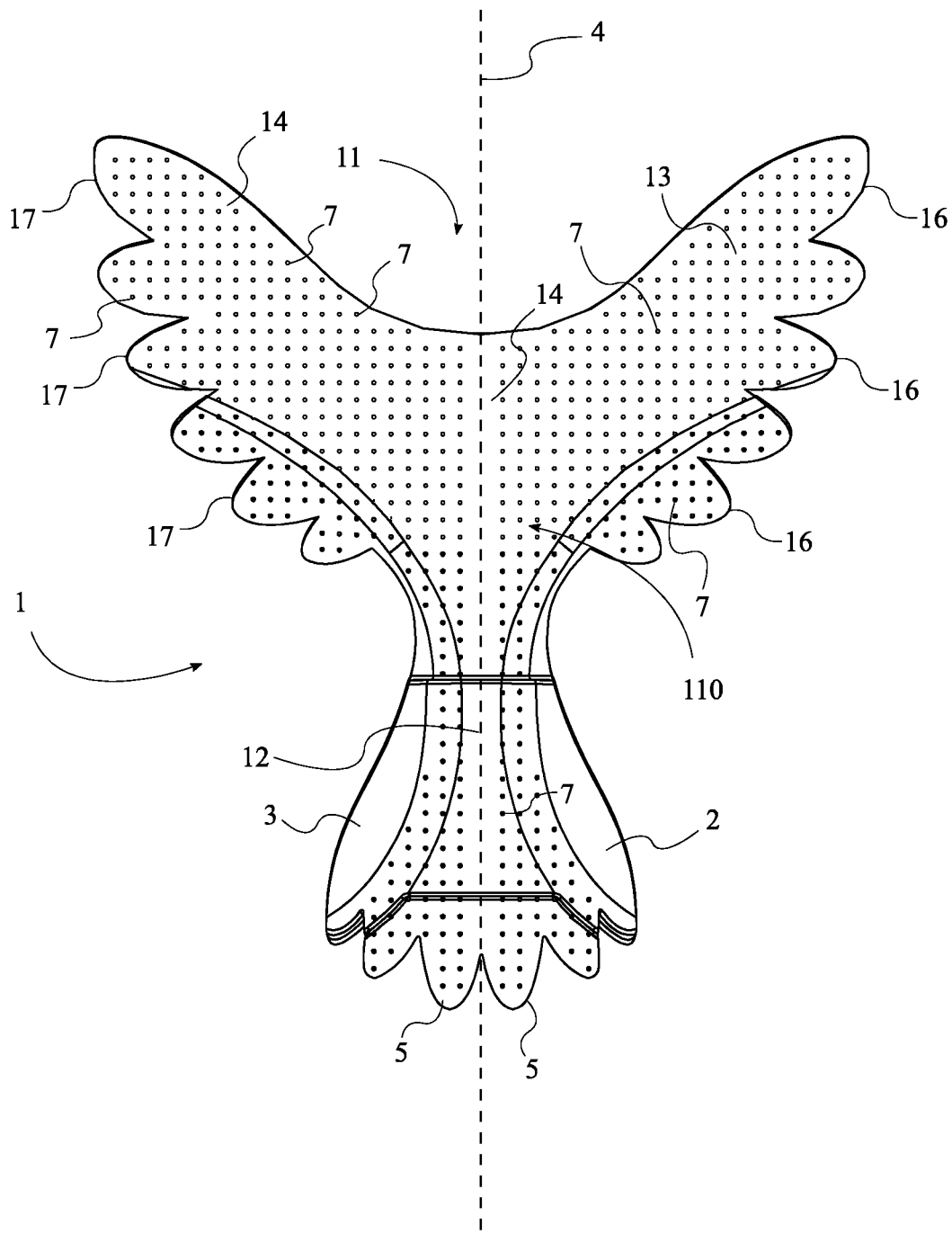
FIG. 2 is a rear view of the present invention.
Figure 3:
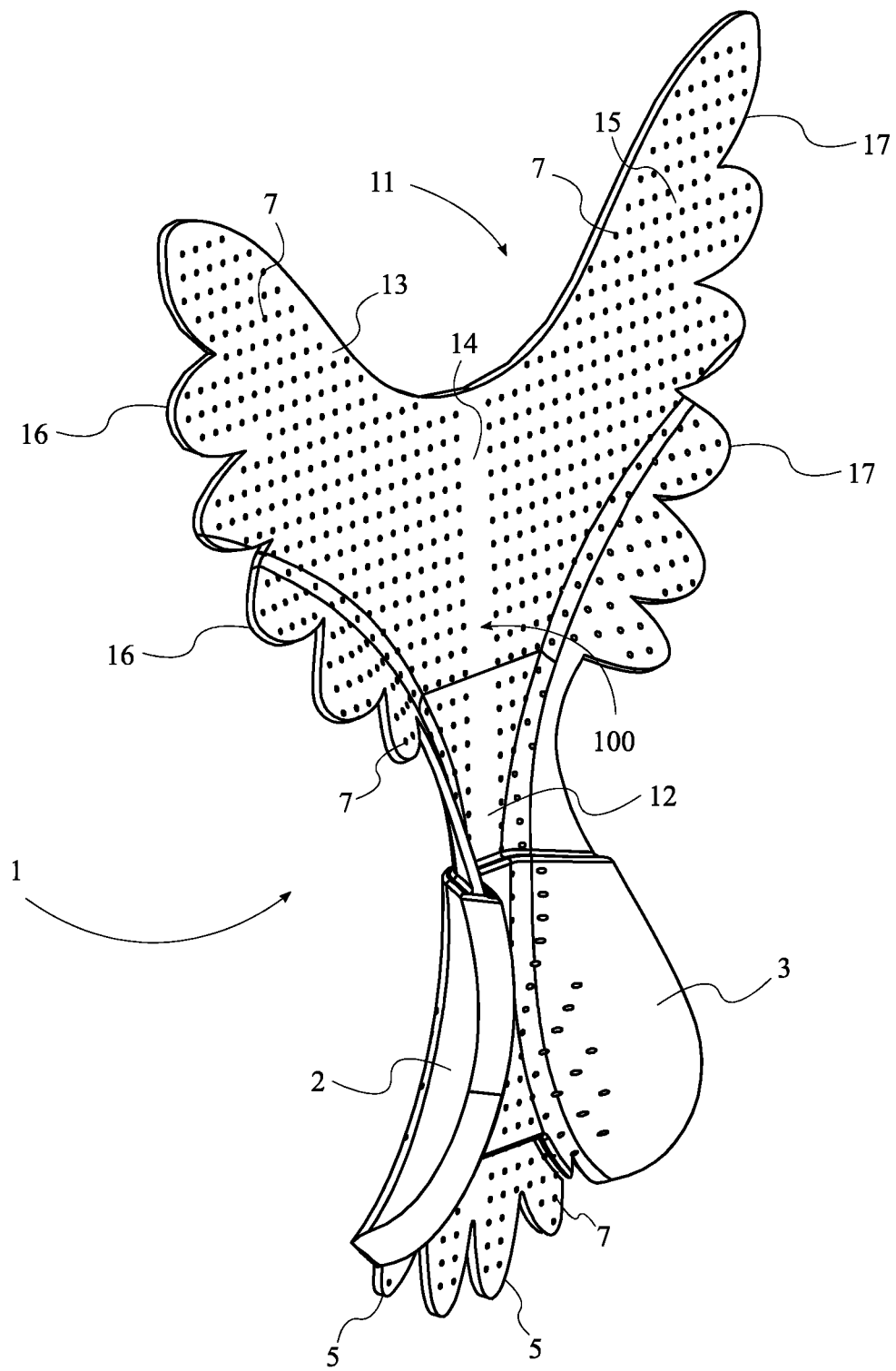
FIG. 3 is a front left perspective view of the present invention.

Referring to FIGS. 1-3, in general, the preferred embodiment of the present invention comprises a support body 1, a first breast support 2, and a second breast support 3, with the support body 1 comprising an upper support portion 11 and a sternum portion 12. In the preferred embodiment, the support body 1 is manufactured of a flexible material and is a generally planar feature, though some curvature of the support body 1 in various forms may be incorporated to better conform to a user's anatomy, in addition to the flexibility of the material of the support body 1. The upper support portion 11 is connected adjacent to the sternum portion 12, positioned above the sternum portion 12 on the user's upper chest while the user is wearing the present invention, forming the majority of the structural body of the present invention.

The upper support portion 11 and the sternum portion 12 are affixed to the user's torso when worn, with the upper support portion 11 being positioned on the user's chest between the breasts and collarbone, and the sternum portion 12 being positioned centrally between the user's breasts on the sternum. Preferably, the upper support portion 11 and the sternum portion 12 are symmetrical about a sagittal plane 4, wherein the sagittal plane 4 may be understood to divide the present invention laterally as shown in FIGS. 1-2. The first breast support 2 is laterally connected to the sternum portion 12, and the second breast support 3 is laterally connected to the sternum portion 12 opposite the first breast support 2, with the first breast support 2 and the second breast support 3 preferably being laterally symmetrical about the sagittal plane 4. It should be noted, however, that the aforementioned symmetry of the present invention is not a required feature, and some embodiments of the present invention may incorporate asymmetry in various forms as desired and applicable, for example for users with asymmetrical anatomy.

The first breast support 2 and the second breast support 3 are generally concave planar features, configured to conform to the lateral inside surfaces of the user's breasts, in order to provide support to the breasts. The first breast support 2 and the second breast support 3 may comprise, in various embodiments, various forms of padding for user comfort.

In some embodiments, the upper support portion 11 comprises a first lateral support portion 13, a medial portion 14, and a second lateral support portion 15. The medial portion 14 is connected adjacent to the sternum portion 12, the first lateral support portion 13 is connected adjacent to the medial portion 14, perpendicular to the sternum portion 12, and the second lateral support portion 15 is connected adjacent to the medial portion 14 opposite the first lateral support portion 13. The sternum portion 12 is laterally aligned with the medial portion 14, between the first lateral support portion 13 and the second lateral support portion 15.

Though it should be noted that the first lateral support portion 13, the medial portion 14, and the second lateral support portion 15 may comprise various shapes and sizes, in the preferred embodiment the first lateral support portion 13 and the second lateral support portion 15 each comprise an elongated, tapered shape resembling a spread wing, tapering upward and laterally outward from the medial portion 14. The purpose of the upper support portion 11 may be regarded as primarily to facilitate adequate attachment and support of the support body 1, thus it is desired that the first lateral portion and the second lateral portion cover a large amount of surface area of the user's chest, though this may be balanced against user comfort in consideration of its dimensions.

Figure 4:
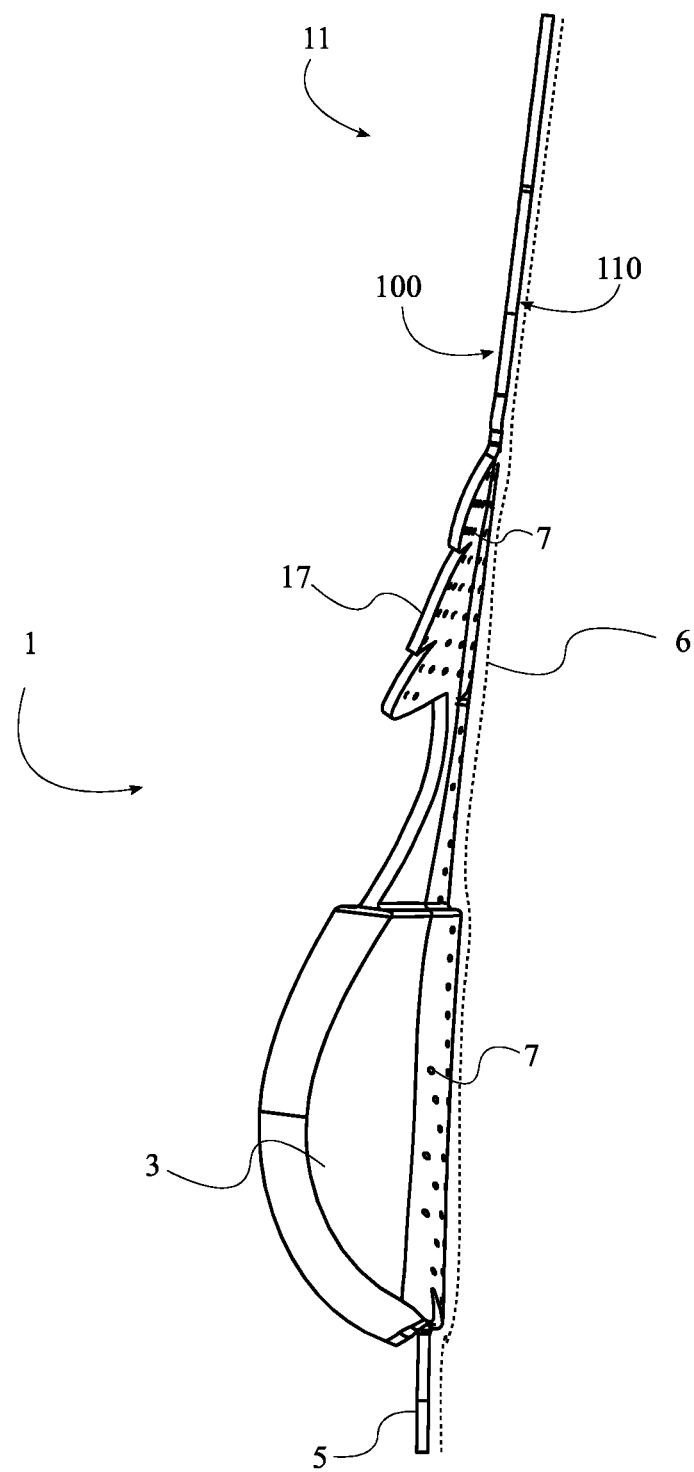
FIG. 4 is a right view of the present invention.

In order to affix the present invention to a user's chest, in the preferred embodiment, the present invention further comprises an adhesive layer 6. Furthermore, the support body 1 comprises a front side 100 and a rear side 110, with the front side 100 and the rear side 110 being positioned opposite each other through the support body 1. The adhesive layer 6 is connected to the rear side 110 of the support body 1 as shown in FIG. 4, so that the rear side 110 is affixed to the user's chest while in use. In various embodiments, the adhesive layer 6 may take various forms. In the preferred embodiment, the adhesive layer 6 is a soft polymer, such as, but not limited to, silicone, with "sticky" material properties that allow the adhesive layer 6 to adhere to the user's skin but also be easily removed. In other embodiments, the adhesive layer 6 may comprise other adhesive means, such as, but not limited to, various types of skin glues or other adhesive means. It should be noted that the adhesive layer 6 is not strictly required to be adhesive in the sense that glue or epoxy-like material is adhesive, and in some embodiments the adhesive layer 6 may simply have a high coefficient of friction with human skin, for example. In some embodiments, the adhesive layer 6 is omitted, and alternative means may be used to affix the present invention to a user's chest, such as, but not limited to, various types and configurations of straps and/or harnesses.

In the preferred embodiment of the present invention, the upper support portion 11 further comprises a first plurality of lateral ridges 16 and a second plurality of lateral ridges 17. The first plurality of lateral ridges 16 is laterally connected to the first lateral support portion 13 opposite the medial portion 14 and is distributed evenly along an external lateral edge of the first lateral support portion 13. Similarly, the second plurality of lateral ridges 17 is laterally connected to the second lateral support portion 15 opposite the medial portion 14 and is distributed evenly along an external lateral edge of the second lateral support portion 15. In the preferred embodiment, the adhesive layer 6 extends on the rear surface to the periphery of each of the first plurality of lateral ridges 16 and the second plurality of lateral ridges 17. The first plurality of lateral ridges 16 and the second plurality of lateral ridges 17 provide additional adhesive support for affixing the present invention to the user's chest.

In a similar vein, the preferred embodiment further comprises a plurality of lower ridges 5. The plurality of lower ridges 5 is connected adjacent to the sternum portion 12 opposite the upper support portion 11, providing additional adhesive support at the lower end of the present invention.

Additionally, the preferred embodiment of the present invention comprises a plurality of perforations 7. The plurality of perforations 7 preferably traverses through the front side 100 and rear side 110 of the support body 1 and is evenly distributed across the support body 1. The plurality of perforations 7 provides ventilation for the skin of the user to breathe while the present invention is worn by the user. In some embodiments, the plurality of perforations 7 comprises 108 perforations. It should be noted that while the word "perforations" is used herein, it may be understood that other terminology may similarly suffice, such as, but not limited to, pores or holes. The plurality of perforations 7 further allows application of ointments, lotions, moisturizers, oils, and the like while the present invention is worn by the user.

Although the invention has been explained in relation to its preferred embodiment, it is to be understood that many other possible modifications and variations can be made without departing from the spirit and scope of the invention as hereinafter claimed.

What is claimed is:

1. A breast support comprises:
   a support body comprising an upper support portion and a sternum portion;
   a first breast support;
   a second breast support;
   the upper support portion being connected adjacent to the sternum portion;
   the first breast support being laterally connected to the sternum portion;
   the second breast support being laterally connected to the sternum portion opposite the first breast support;
   a plurality of lower ridges; and
   the plurality of lower ridges being connected adjacent to the sternum portion opposite the upper support portion.

2. The breast support as claimed in claim 1 comprises:
   the upper support portion and the sternum portion being symmetrical about a sagittal plane.

3. The breast support as claimed in claim 1 comprises:
   the upper support portion comprises a first lateral support portion, a medial portion, and a second lateral support portion;
   the medial portion being connected adjacent to the sternum portion;
   the first lateral support portion being connected adjacent to the medial portion;
   the second lateral support portion being connected adjacent to the medial portion opposite the first lateral support portion; and
   the sternum portion being laterally aligned with the medial portion, between the first lateral support portion and the second lateral support portion.

4. The breast support as claimed in claim 3 comprises:
   the upper support portion further comprises a first plurality of lateral ridges and a second plurality of lateral ridges;
   the first plurality of lateral ridges being laterally connected to the first lateral support portion opposite the medial portion; and
   the second plurality of lateral ridges being laterally connected to the second lateral support portion opposite the medial portion.

5. The breast support as claimed in claim 1 comprises:
an adhesive layer;
the support body comprises a front side and a rear side;
the front side and the rear side being positioned opposite each other through the support body; and
the adhesive layer being connected to the rear side.

6. The breast support as claimed in claim 1 comprises:
a plurality of perforations;
the plurality of perforations traversing through a front side and a rear side of the support body; and
the plurality of perforations being distributed across the support body.

7. The breast support as claimed in claim 1 comprises:
the support body being manufactured of a flexible material.

* * * * *